(12) United States Patent  
Kato et al.

(10) Patent No.: US 11,990,954 B2  
(45) Date of Patent: May 21, 2024

(54) WEARABLE KEY DEVICE AND ELECTRONIC KEY SYSTEM

(71) Applicant: DENSO CORPORATION, Kariya (JP)

(72) Inventors: Yoichi Kato, Kariya (JP); Takeshi Kumazaki, Kariya (JP); Kenji Kato, Kariya (JP)

(73) Assignee: DENSO CORPORATION, Aichi-pref. (JP)

( * ) Notice: Subject to any disclaimer, the term of this patent is extended or adjusted under 35 U.S.C. 154(b) by 905 days.

(21) Appl. No.: 17/004,866

(22) Filed: Aug. 27, 2020

(65) Prior Publication Data

US 2020/0391696 A1  Dec. 17, 2020

Related U.S. Application Data

(63) Continuation of application No. PCT/JP2019/001691, filed on Jan. 21, 2019.

(30) Foreign Application Priority Data

Mar. 1, 2018  (JP) .................................. 2018-036869

(51) Int. Cl.
*H04B 5/72*  (2024.01)
*B60R 25/24*  (2013.01)
(Continued)

(52) U.S. Cl.
CPC ............. *H04B 5/72* (2024.01); *B60R 25/241* (2013.01); *B60R 25/25* (2013.01); *G06F 18/22* (2023.01);
(Continued)

(58) Field of Classification Search
CPC ...... H04B 5/0031; H04B 5/72; B60R 25/241; B60R 25/25; B60R 2325/103;
(Continued)

(56) References Cited

U.S. PATENT DOCUMENTS

2009/0110249 A1* 4/2009 Miura .................... G06V 40/12  
                                           382/124  
2009/0249478 A1* 10/2009 Rosener ................. G06F 21/31  
                                           726/19

(Continued)

FOREIGN PATENT DOCUMENTS

JP         H1193478 A      4/1999  
JP     2007328485 A *  12/2007  
(Continued)

*Primary Examiner* — Philip J Chea  
*Assistant Examiner* — Sangseok Park  
(74) *Attorney, Agent, or Firm* — Harness, Dickey & Pierce, P.L.C.

(57) ABSTRACT

A wearable key device is to be used while being worn on a predetermined position of a body and includes a ring communication module, an imaging device, and a ring controller. The ring communication module is configured to wirelessly communicate with an authentication device provided to a predetermined protection object. The imaging device is configured to capture an image of the predetermined position of the body. The ring controller is configured to acquire wearer information that is biometric information of a wearer who wears the wearable key device based on the image captured by the imaging device. The wearer information is used for determining whether the wearer is an authorized user.

16 Claims, 8 Drawing Sheets

(51) Int. Cl.
   *B60R 25/25*   (2013.01)
   *G06F 18/22*   (2023.01)
   *G06F 21/32*   (2013.01)
   *G06V 40/10*   (2022.01)
   *G08B 7/06*    (2006.01)
   *H04N 23/57*   (2023.01)
   *G06V 40/12*   (2022.01)
   *G06V 40/14*   (2022.01)

(52) U.S. Cl.
   CPC .............. *G06F 21/32* (2013.01); *G06V 40/10* (2022.01); *G08B 7/06* (2013.01); *H04N 23/57* (2023.01); *B60R 2325/103* (2013.01); *G06V 40/1341* (2022.01); *G06V 40/14* (2022.01)

(58) Field of Classification Search
   CPC ......... G06F 18/22; G06F 21/32; G06V 40/10; G06V 40/1341; G06V 40/14; G08B 7/06; H04N 23/57; A61B 5/1171; E05B 49/00
   See application file for complete search history.

(56) References Cited

U.S. PATENT DOCUMENTS

| | | | |
|---|---|---|---|
| 2018/0082050 A1* | 3/2018 | Flink | H04L 9/3228 |
| 2018/0234415 A1* | 8/2018 | Fukuda | A61B 5/1171 |
| 2018/0272991 A1* | 9/2018 | Tayama | B60R 25/252 |

FOREIGN PATENT DOCUMENTS

| | | |
|---|---|---|
| JP | 2010211433 A | 9/2010 |
| JP | 2013061946 A | 4/2013 |
| JP | 5400407 B2 | 1/2014 |
| JP | 2015109939 A | 6/2015 |
| JP | 2017043267 A | 3/2017 |
| WO | WO-2017026446 A1 | 2/2017 |

* cited by examiner

⇐ : IRRADIATION DIRECTION OF LIGHT EMITTING MODULE

⇐ : IRRADIATION DIRECTION OF LIGHT EMITTING MODULE

WEARABLE KEY DEVICE AND ELECTRONIC KEY SYSTEM

CROSS REFERENCE TO RELATED APPLICATIONS

The present application is a continuation application of International Patent Application No. PCT/JP2019/001691 filed on Jan. 21, 2019, which designated the U.S. and claims the benefit of priority from Japanese Patent Application No. 2018-036869 filed on Mar. 1, 2018. The entire disclosures of all of the above applications are incorporated herein by reference.

TECHNICAL FIELD

The present disclosure relates to a wearable key device and an electronic key system.

BACKGROUND

Conventionally, there has been known an electronic key system that performs wireless communication between an authentication device provided to a protection object such as a vehicle or a residential facility and an electronic key carried by a user to set a locking mechanism of the protection object to be an unlocked state or a locked state.

SUMMARY

The present disclosure provides a wearable key device and an electronic key system that includes the wearable key device and an authentication device provided to a predetermined protection object. The wearable key device is to be used while being worn on a predetermined position of a body and includes a ring communication module, an imaging device, and a ring controller. The ring communication module is configured to wirelessly communicate with the authentication device. The imaging device is configured to capture an image of the predetermined position of the body. The ring controller is configured to acquire wearer information that is biometric information of a wearer who wears the wearable key device based on the image captured by the imaging device. The wearable information can be used for determining whether the wearer is an authorized user.

BRIEF DESCRIPTION OF DRAWINGS

Objects, features and advantages of the present disclosure will become apparent from the following detailed description made with reference to the accompanying drawings. In the drawings.

DETAILED DESCRIPTION

Figure 1:
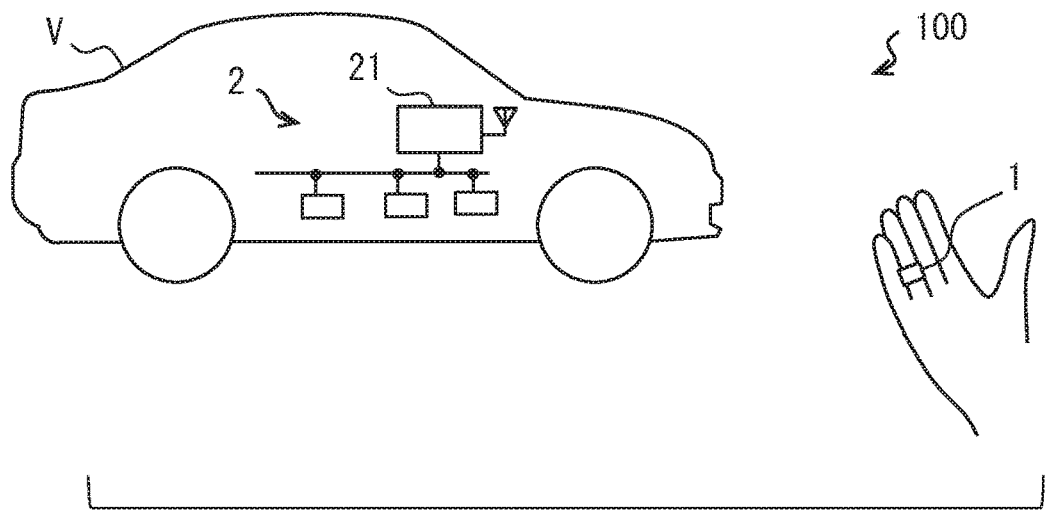
FIG. 1 is a block diagram showing a schematic configuration of a vehicle electronic key system.

There is an electronic key system for a vehicle that performs an authentication process by wireless communication between an authentication device mounted on the vehicle and a portable device (so-called smart key) carried by a user, and performs a vehicle control such as locking and unlocking of vehicle doors or starting of an engine when the authentication process is successful.

In the above electronic key system, a person who is not an authorized user of the vehicle (hereinafter, a third party) can also use the vehicle as long as they have the portable device as an electronic key. Therefore, if a user drops the portable device or the portable device is stolen, the vehicle may be illegally used.

Such an issue may occur also in an electronic key system for a house. When a portable device that functions as a key of a protection object such as a vehicle or a house is passed into a third party's hand, there is a fear the locked state of the protection object is released by the third party and the protection object is illegally used.

A wearable key device according to a first aspect of the present disclosure is to be used while being worn on a predetermined position of a body, and includes a ring communication module, an imaging device, a user information storage, and a ring controller. The ring communication module is configured to wirelessly communicate with an authentication device provided to a predetermined protection object. The imaging device is configured to capture an image of the predetermined position of the body. The user information storage stores user information that is biometric information of an authorized user. The ring controller is configured to cooperate with the ring communication module and transmit, to the authentication device, authentication information that is information for certifying that the wearable key device is a key of the protection object, acquire wearer information that is biometric information of a wearer who wears the wearable key device based on the image captured by the imaging device, and compare the wearer information and the user information stored by the user information storage to determine whether the wearer is the authorized user. The ring controller is further configured to transmit the authentication information in response to a request from the authentication device when determining that the wearer is the authorized user, and not to transmit the authentication information when not determining that the wearer is the authorized user.

When determining that the wearer is the authorized user as a result of the user authentication process using the biometric information, the wearable key device transmits the predetermined authentication information to the authentication device. On the other hand, when determining that the wearable key device is not worn by the authorized user as a result of the user authentication process, the wearable key device does not transmit the authentication information to the authentication device. Therefore, the authentication of the wearable key device by the authentication device fails.

With such a configuration, even if a third party obtains the wearable key device, the third party cannot use the protection object using the wearable key device. Therefore, even if the user drops the wearable key device or the wearable key device is stolen, it is possible to reduce the risk that the protection object is illegally used.

An electronic key system according to a second aspect of the present disclosure includes a wearable key device configured to be used while being worn on a predetermined position of a body and an authentication device configured to be provided to a predetermined protection object. The wearable key device includes a ring communication module configured to perform wireless communication with the authentication device, an imaging device configured to capture an image of the predetermined position of the body, and a ring controller configured to acquire wearer information that is biometric information of a wearer who wears the wearable key device based on the image captured by the imaging device and transmit the wearer information to the authentication device by cooperating with the ring communication module. The authentication device is connected with an authentication side communication module configured to perform the wireless communication with the wearable key device. The authentication device includes a user information storage storing user information that is biometric information of an authorized user, and an authentication processor configured to acquire the wearer information from the wearable key device by cooperating with the authentication side communication module, determine whether the wearer is the authorized user by comparing the wearer information and the user information stored by the user information storage, and perform a predetermined control to use the protection object when determining that the wearer is the authorized user.

According to the above configuration, the authentication device acquires the wearer information read by the wearable key device by the wireless communication, and compares the wearer information with the user information registered in advance in the authentication device to perform the authentication of the wearer. Then, when it is determined that the wearer is not the authorized user, a control (for example, unlocking) for the wearer to use the protection object is not performed.

With such a configuration, even if a third party obtains the wearable key device, the third party cannot use the wearable key device to use the protection object. That is, it is possible to reduce the risk that the protection object is illegally used.

A wearable key device according to a third aspect of the present disclosure is to be used while being worn on a predetermined position of a body, and includes a ring communication module configured to wirelessly communicate with an authentication device provided to a predetermined protection object, an imaging device configured to capture an image of the predetermined position of the body, and a ring controller configured to acquire wearer information that is biometric information of a wearer who wears the wearable key device based on the image captured by the imaging device and transmit the wearer information as information for determining whether the wearer is an authorized user to the authentication device by cooperating with the ring communication module.

The wearable key device having the above configuration is the wearable key device configuring the above electronic key system according to the second aspect. That is, according to the wearable key device having the above configuration, it is possible to reduce the risk of unauthorized use of the protection object by cooperating with the authentication device separately provided to the protection object.

Embodiments of the present disclosure will be described below with reference to the drawings. FIG. 1 is a diagram showing an example of a schematic configuration of a vehicle electronic key system according to an embodiment. As shown in FIG. 1, the vehicular electronic key system includes an in-vehicle system 2 mounted on a vehicle V, and a smart ring 1 worn by a user of the vehicle V when used. The vehicle V is an example of a protection object. The smart ring 1 is an example of a wearable key device.

The smart ring 1 is a ring-type device that is worn on a user's finger when used. The smart ring 1 is associated with the in-vehicle system 2 and has a function as a key (specifically, an electronic key) of the vehicle V. A finger on which the smart ring 1 is worn is predetermined by the user or the like to one finger, for example, the ring finger (that is, the third finger) of the right hand. The diameter of the smart ring 1 is set to a size corresponding to the thickness of the predetermined finger of the user. Among the plurality of fingers of the user, the finger predetermined as the finger on which the smart ring 1 is worn is an example of a predetermined position of a body.

In the present embodiment, the vehicle V is assumed to be an engine vehicle including only an engine as a power source, but is not limited to the engine vehicle. The vehicle V may be a so-called hybrid vehicle including an engine and a motor as a power source, or an electric vehicle including only a motor as a power source. The vehicle V may be a vehicle having an autonomous driving function.

The smart ring 1 and the in-vehicle system 2 are each configured to be capable of performing wireless communication according to a near-field communication (NFC) standard. Near-field communication here refers to communication in which a communicable distance is from several cm to several tens of cm. As a specific communication standard for realizing near-field communication, various standards such as ISO/IEC 14443 and ISO/IEC 18092 can be adopted.

The in-vehicle system 2 is configured to perform near-field communication with the smart ring 1 to perform processing for confirming that a person using the vehicle V is an authorized user, and to perform a predetermined vehicle control. The vehicle control that can be performed by the in-vehicle system 2 includes unlocking and locking of a vehicle door, starting of an engine, and the like. Hereinafter, for convenience, the function of the in-vehicle system 2 automatically (or semi-automatically) performing predetermined vehicle control based on the result of wireless communication between the in-vehicle system 2 and the smart ring 1 is also referred to as a smart function.

Figure 2:
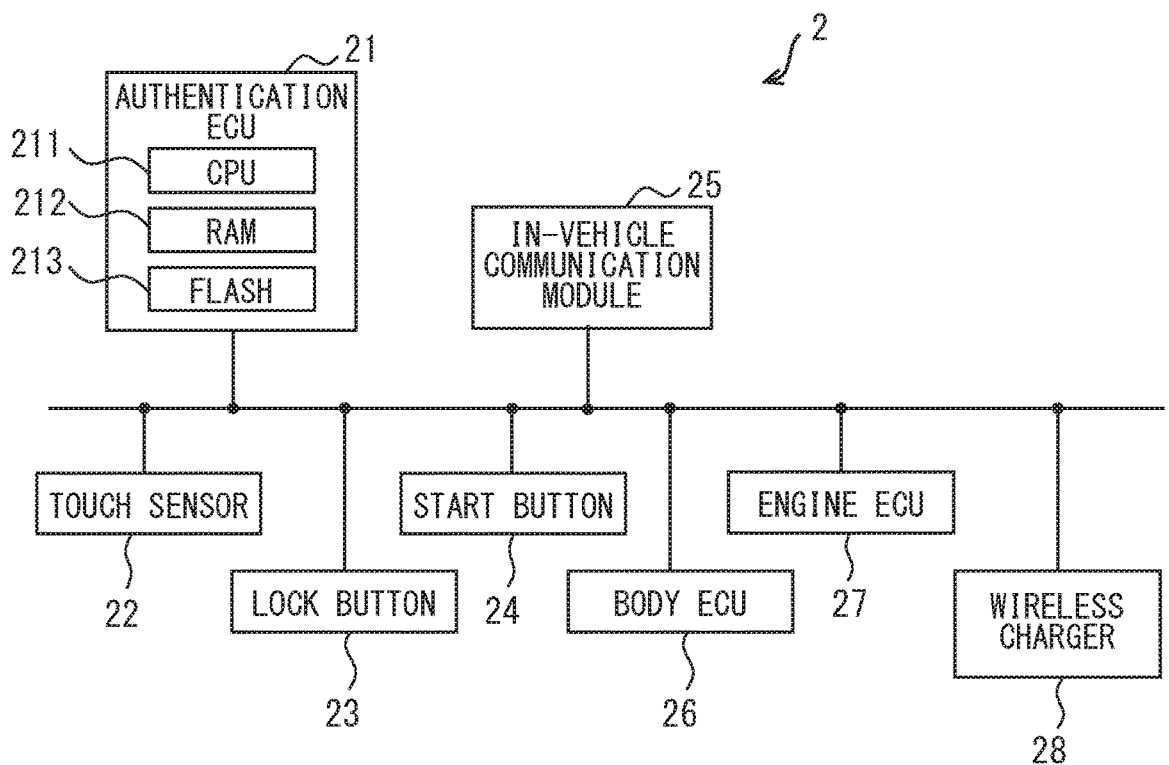
FIG. 2 is a block diagram showing an electrical configuration of an in-vehicle system.

As shown in FIG. 2, the in-vehicle system 2 includes an authentication ECU 21, a touch sensor 22, a lock button 23, a start button 24, an in-vehicle communication module 25, a body ECU 26, an engine ECU 27, and a wireless charger 28.

The authentication ECU 21 is an electronic control unit (ECU) that executes various processes for providing the smart function described above. The authentication ECU 21 is an example of an authentication device. The authentication ECU 21 is communicatively connected with each of the touch sensor 22, the lock button 23, the start button 24, the in-vehicle communication module 25, the body ECU 26, the engine ECU 27, and the wireless charger 28 via a communication network built in the vehicle V. The in-vehicle communication module 25 may be connected to the authentication ECU 21 via a dedicated signal line. The same applies to the touch sensor 22, the lock button 23, the start button 24, and the like.

The authentication ECU 21 is configured as a normal computer including a central processing unit (CPU) 211, a random access memory (RAM) 212, a flash memory 213, an input-output device (I/O), and a bus line connecting these components. The authentication ECU 21 may be implemented by use of a graphical processing unit (GPU) or a microprocessor unit (MPU) instead of the CPU 211. The authentication ECU 21 may also be realized by a combination of a CPU, a GPU, and an MPU. The CPU 211 is an example of an authentication processor.

The flash memory 213 is a non-volatile and rewritable memory. The flash memory 213 stores a program for causing a normal computer to function as the authentication ECU 21 (hereinafter, authentication program) and the like. As a concrete storage medium for storing the authentication program, various non-transitional substantive storage medium can be adopted. Executing the authentication program by the CPU 211 corresponds to executing a method corresponding to the authentication program. The flash memory 213 is an example of an authentication memory.

The authentication ECU 21 generates data to be transmitted to the smart ring 1 and outputs the data to the in-vehicle communication module 25. In addition, the authentication ECU 21 acquires the data received by the in-vehicle communication module 25. The authentication ECU 21 executes processing on the vehicle side for realizing the smart function by executing the authentication program by the CPU 211. Details of the authentication ECU 21 will be described later.

The touch sensor 22 is installed in each door handle of the vehicle V and detects that the user touches the door handle. The detection result of each touch sensor 22 is sequentially output to the authentication ECU 21. For example, when the touch sensor 22 is touched by the user, the touch sensor 22 outputs an ON signal. On the other hand, when the touch sensor 22 is not touched by the user, the touch sensor 22 outputs an OFF signal. The touch sensor 22 is an example of a configuration for the authentication ECU 21 to receive unlocking instructions from the user.

The lock button 23 is a button for the user to lock the door of the vehicle V. The lock button 23 may be provided on each door handle of the vehicle V. When the user presses the lock button 23, the lock button 23 outputs a control signal indicative of this fact to the authentication ECU 21. The lock button 23 may have a function as a button for accepting unlocking instructions from the user instead of the touch sensor 22. That is, the lock button 23 may be configured as a button for the authentication ECU 21 to receive unlocking instructions and locking instructions from the user. In that case, the touch sensor 22 can be omitted.

The start button 24 is a push switch for the user to start the engine. When the user performs a push operation on the start button 24, the start button 24 outputs an electric signal indicating the push operation to the authentication ECU 21.

The in-vehicle communication module 25 is a communication module for performing near-field communication (in other words, NFC communication) with the smart ring 1. The in-vehicle communication module 25 is an example of an authentication side communication module.

The in-vehicle communication module 25 converts the data input from the authentication ECU 21 into a radio signal having a frequency (for example, 13.56 MHz) set as a carrier frequency in the NFC standard, and radiates the radio signal into space. In addition, the in-vehicle communication module 25 receives a wireless signal transmitted from the smart ring 1, performs a predetermined reception process such as demodulation on the received signal to obtain data, and provides the data to the authentication ECU 21.

The in-vehicle communication module 25 is provided at a predetermined position of the vehicle V. It is preferable that the in-vehicle communication module 25 is provided at a position where the in-vehicle communication module 25 can perform near-field communication with the smart ring 1 attached to the user's finger when a user operation for locking and unlocking the vehicle V is performed or when a user operation for starting the engine is performed.

Figure 3:
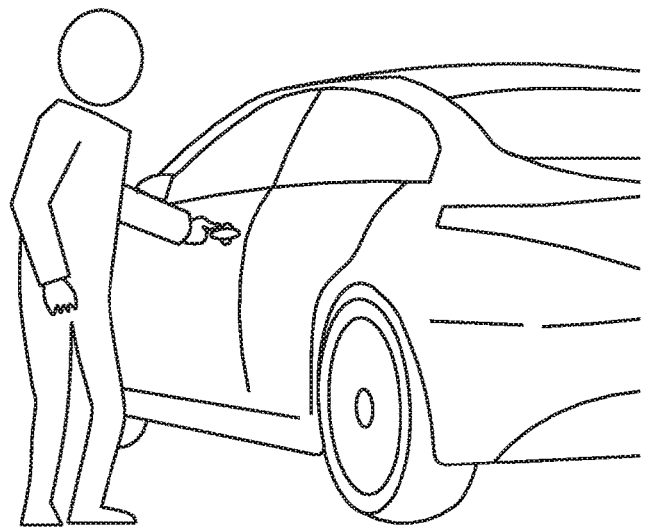
FIG. 3 is a diagram for explaining an operation example of the in-vehicle system when an in-vehicle communication module is provided to a door handle.

In the present embodiment, as an example, the in-vehicle communication module 25 is provided near each door handle of the vehicle V and the start button 24. According to the configuration in which the in-vehicle communication module 25 is provided to the door handle, the in-vehicle communication module 25 and the smart ring 1 can communicate with each other when the user touches the touch sensor 22, presses the lock button 23, or grips the door handle as illustrated in FIG. 3. That is, when the user performs an operation for locking and unlocking the vehicle V, the in-vehicle communication module 25 and the smart ring 1 can communicate with each other.

Further, according to the configuration in which the in-vehicle communication module 25 is provided near the start button 24, the in-vehicle communication module 25 and the smart ring 1 can communicate with each other when a user operation for starting the engine is performed. The user operation for starting the engine in the present embodiment is a pressing operation of the start button 24. The in-vehicle communication module 25 may be provided, for example, on a steering wheel or in a grip portion of a shift lever, instead of the above-described positions. The installation position of the in-vehicle communication module 25 can be appropriately changed in consideration of user convenience, communication stability, and the like.

The body ECU 26 is an ECU that controls various actuators mounted on the vehicle V. For example, the body ECU 26 outputs a drive signal for controlling the locking and unlocking of the door provided on the vehicle V to a door lock motor provided on each of the vehicle doors based on an instruction from the authentication ECU 21, to lock and unlock each of the doors. In addition, the body ECU 26 acquires information indicating an open and close state of each of the doors provided in the vehicle, information indicating a locked or unlocked state of each of the doors, and the like. Note that the open and close state of the door may be detected by a courtesy switch.

The engine ECU 27 is an ECU that controls the operation of the engine. For example, when the engine ECU 27 acquires a start instruction signal that instructs starting of the engine from the authentication ECU 21, the engine ECU 27 starts the engine.

The wireless charger 28 is a device on a power transmission side for wirelessly charging the smart ring 1 using electromagnetic waves in a predetermined frequency band. As a standard for wireless charging, various standards such as a standard defined by Wireless Power Consortium (WPC) (so-called Qi standard) and the AirFuel Inductive defined by the AirFuel (Trademark) Alliance can be adopted. The AirFuel Inductive corresponds to a standard established by the Power Matters Alliance (PMA). The wireless charger 28 is realized by using a primary coil for providing electric power as electromagnetic waves by electromagnetically coupling with a secondary coil included in the smart ring 1. The wireless charger 28 is disposed, for example, in a steering hole of the vehicle V. According to the configuration in which the wireless charger 28 is disposed in the steering hole, a battery 16 included in the smart ring 1 is charged by the wireless charger 28 while the user performs driving operation. As a result, the convenience of the user can be improved.

Figure 4:
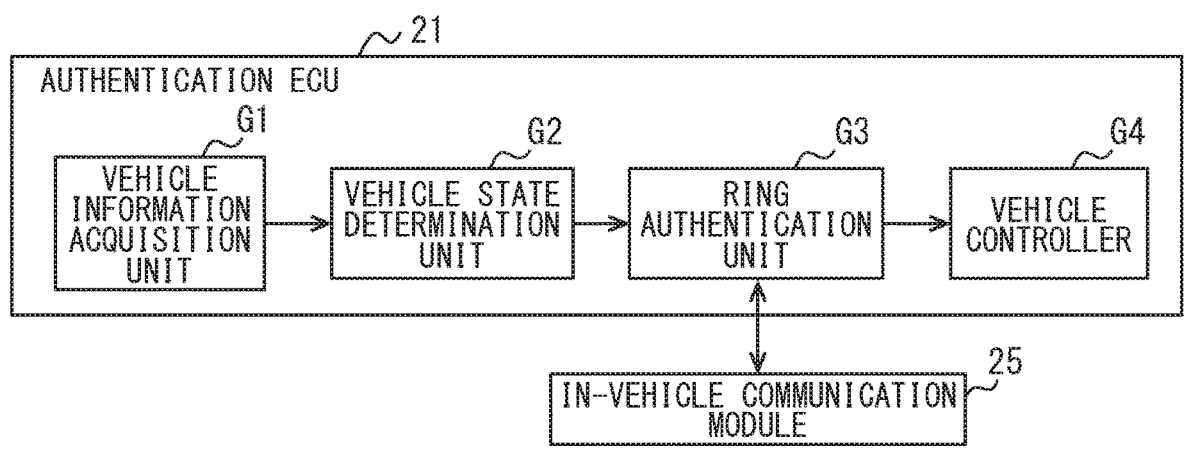
FIG. 4 is a functional block diagram of an authentication ECU.

As shown in FIG. 4, the authentication ECU 21 includes a vehicle information acquisition unit G1, a vehicle state determination unit G2, a ring authentication unit G3 and a vehicle controller G4 as functional blocks realized by the CPU 211 executing the above-described authentication side program. Some or all of the functions of the authentication ECU 21 may be realized as hardware. A configuration in which a certain function is realized as hardware includes a configuration in which the function is realized by use of one or more ICs or the like.

The vehicle information acquisition unit G1 acquires various information (that is, vehicle information) indicating a state of the vehicle V from sensors such as the touch sensor 22 and an ECU mounted on the vehicle. The vehicle information is indicative of, for example, whether the user touches the door handle, the door opening and closing state, whether the brake pedal is depressed, whether the start button 24 is pressed, and whether each door is locked.

Whether the user touches the door handle can be acquired from the touch sensor 22 and whether the start button 24 is pressed can be determined according to a signal output from the start button 24. The opening and closing states of the doors, the locking and unlocking states of the doors, and the like can be acquired from the body ECU 26, for example. Note that the opening and closing states of the doors may be detected by a courtesy switches. Whether the brake pedal is depressed can be detected by a brake pedal sensor that detects the amount of depression of the brake pedal by the user. The information included in the vehicle information is not limited to the above-described information. A shift position detected by a shift position sensor, which is not shown, an operation state of a parking brake, and so on may also be included in the vehicle information.

The vehicle state determination unit G2 determines a condition of the vehicle V based on the vehicle information acquired by the vehicle information acquisition unit G1. The vehicle state determination unit G2 determines whether the vehicle V is parked based on the vehicle information acquired by the vehicle information acquisition unit G1. For example, the vehicle state determination unit G2 determines that the vehicle is parked when all the doors are locked in a state where the engine is off and all the doors are closed. It is needless to say that various algorithms can be employed as a determination algorithm for determining whether the vehicle is parked.

The ring authentication unit G3 cooperates with the in-vehicle communication module 25 to perform a ring authentication processing. The ring authentication process here is a process for confirming that a communication terminal wirelessly communicating with the in-vehicle system 2 is the smart ring 1 associated with the vehicle V. The successful authentication corresponds to the determination that the communication partner of the in-vehicle communication module 25 is the regular smart ring 1.

As the authentication method of the smart ring 1 by the ring authentication unit G3, various methods can be adopted. Here, as an example, the ring authentication unit G3 and the smart ring 1 are configured to perform the authentication process by a challenge-response method. That is, the ring authentication unit G3 transmits an authentication request signal including a challenge code in cooperation with the in-vehicle communication module 25, triggered by the occurrence of a predetermined event for executing the ring authentication process.

The challenge code is a code for authenticating the smart ring 1. The challenge code may be a random number generated with the use of a random number table or the like. As will be described later, when the smart ring 1 receives the challenge code, the smart ring 1 encrypts the challenge code with a previously registered encryption key and returns a signal (hereinafter referred to as a response signal) including the encrypted code (hereinafter referred to as a response code).

In addition to transmit the challenge signal, the ring authentication unit G3 generates a code (hereinafter referred to as a verification code) obtained by encrypting the challenge code using the encryption key held by the ring authentication unit G3. Then, when the returned response code matches the verification code, the ring authentication unit G3 determines that the communication partner is the regular smart ring 1 (that is, the authentication is successful). The response signal is an example of authentication information that is information for certifying that the smart ring 1 is the key of the vehicle V.

The timing at which the ring authentication unit G3 executes the ring authentication process may be appropriately designed. For example, the ring authentication unit G3 may execute the ring authentication process when detecting that the touch sensor 22 is touched by the user, when the lock button 23 is pressed by the user, or when the start button 24 is pressed by the user. The occurrence of an event such as the pressing of the lock button 23 by the user is detected by the vehicle state determination unit G2.

The vehicle controller G4 is configured to perform vehicle control according to the state of the vehicle V or a user operation based on the success of the authentication process by the ring authentication unit G3. The vehicle controller G4 corresponds to a control execution unit. For example, the vehicle controller G4 sets the door lock mechanism of the vehicle V to the unlocked state when the ring authentication process is successful in a state where the doors of the vehicle V are locked. Further, the vehicle controller G4 starts the engine in cooperation with the engine ECU 27 when the ring authentication process is successful in a state where the engine is stopped. In addition, the content of the vehicle control performed by the vehicle controller G4 is appropriately designed in accordance with a scene (in other words, the state of the vehicle V) when the authentication process is successful.

Figure 5:
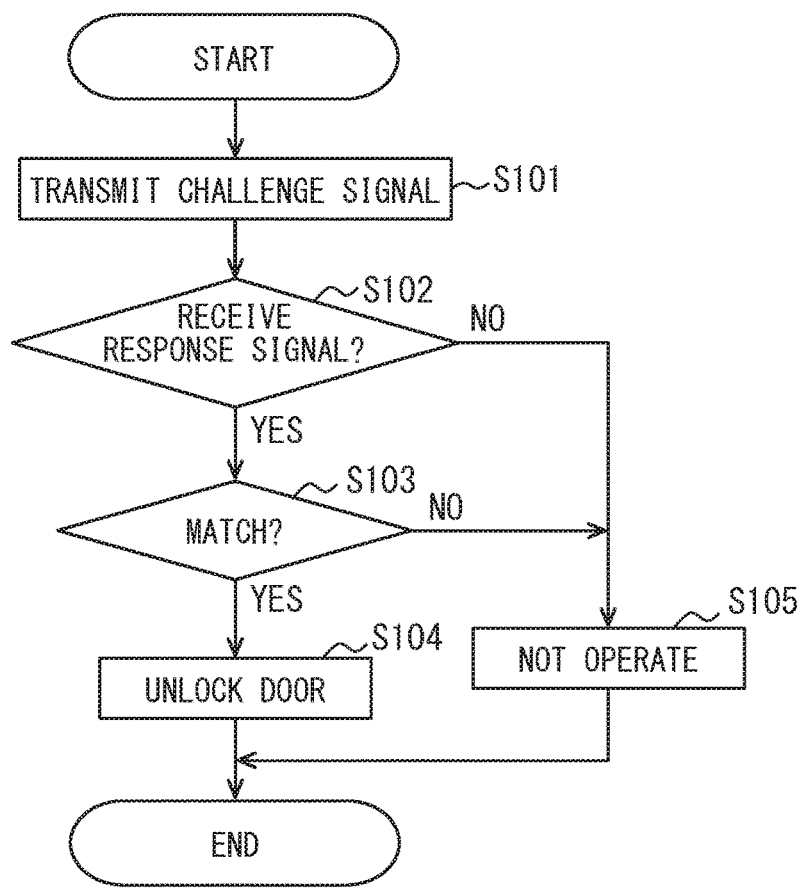
FIG. 5 is a flowchart showing an example of an operation of the authentication ECU.

FIG. 5 is a flowchart showing an operation example of the authentication ECU 21 when the touch sensor 22 is turned on. The flowchart shown in FIG. 5 may be started when the touch sensor 22 is turned on. Each step included in the flowchart shown in FIG. 5 is executed by the authentication ECU 21.

First, in S101, the authentication ECU 21 instructs the in-vehicle communication module 25 to transmit a challenge signal, and the process proceeds to S102. The in-vehicle communication module 25 that transmits the challenge signal in S101 may be the in-vehicle communication module 25 that corresponds to the touch sensor 22 that detects the touch operation by the user. The in-vehicle communication module 25 corresponding to the touch sensor 22 that detects the touch operation by the user is the in-vehicle communication module 25 provided near the touch sensor 22 (for example, the same door handle).

In S102, the authentication ECU 21 determines whether a response signal to the challenge signal transmitted in S101 has been received. When the response signal to the challenge signal transmitted in S101 has been received, an affirmative decision is made in S102 and S103 is executed. On the other hand, when the response signal has not been received even after the lapse of a predetermined response waiting time after the challenge signal is transmitted in S101, a negative determination is made in S102 and the process proceeds to S105.

In S103, the authentication ECU 21 compares the response code included in the response signal received in S102 with the verification code to determine whether the codes match with each other. When the response code and the verification code match with each other, the authentication ECU 21 determines that the communication partner is the smart ring 1 associated with the vehicle V (that is, the authentication is OK), and executes S104. On the other hand, when the response code and the verification code do not match with each other, the authentication ECU 21 determines that the communication partner is not the smart ring 1 associated with the vehicle V (that is, the authentication is NG), and the process proceeds to S105.

In S104, the authentication ECU 21 sets the lock mechanism for the doors of the vehicle V to be the unlocked state in cooperation with the body ECU 26, and ends the present flow. In S105, the authentication ECU 21 maintains the lock mechanism of the doors of the vehicle V in the locked state, and ends the present flow. That is, in S105, the authentication ECU 21 does not perform the vehicle control for unlocking the vehicle doors.

Figure 6:
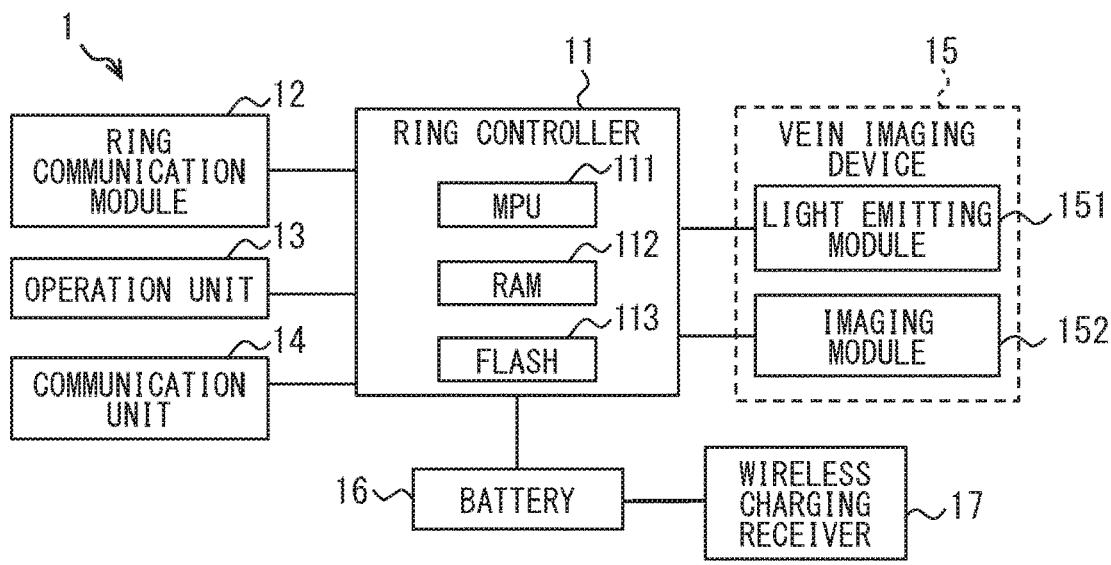
FIG. 6 is a block diagram showing an electrical configuration of a smart ring.

Next, the configuration of the smart ring 1 will be described with reference to the block diagram shown in FIG. 6. As shown in FIG. 6, the smart ring 1 includes a ring controller 11, a ring communication module 12, an operation unit 13, a notification unit 14, a vein imaging device 15, a battery 16, and a wireless charging receiver 17. The ring controller 11 is configured to control the operation of the smart ring 1.

The ring controller 11 is electrically connected to each of the ring communication module 12, the operation unit 13, the vein imaging device 15, the battery 16, and the wireless charging receiver 17. The ring controller 11 is configured as a microcomputer including an MPU 111, a RAM 112, a flash memory 113, and a bus line connecting these components. The ring controller 11 may be realized by using a CPU or GPU instead of the MPU 111. Furthermore, the ring controller 11 may be realized by using one or more dedicated ICs. The functions of the ring controller 11 will be described later.

The flash memory 213 is a non-volatile and rewritable memory. The flash memory 113 stores a program (hereinafter, an electronic key program) for causing a normal microcomputer to function as the ring controller 11, for example. As a concrete storage medium for storing the electronic key program, various non-transitional substantive storage medium can be adopted. Executing the electronic key program by the MPU 111 corresponds to executing a method corresponding to the electronic key program. Further, in the flash memory 113, a vein pattern of the user's finger, which is set as the finger to be attached with the smart ring 1, has been registered (stored) as a user pattern. The vein pattern corresponds to data indicating a pattern of the vehicle (in other words, vein structure). The user pattern is preferably encrypted and stored so that it cannot be referred to by a person who illegally obtained the smart ring 1. The flash memory 113 is an example of a user information storage and is also an example of a ring memory. The MPU 11 is an example of a ring processor.

The ring communication module 12 is a communication module for performing the near-field communication with the in-vehicle system 2. The ring communication module 12 converts the data input from the ring controller 11 into the radio signal having a predetermined frequency and radiates the radio signal into space. In addition, The ring communication module 12 receives the wireless signal transmitted from the in-vehicle system 2, performs the predetermined reception process such as demodulation on the received signal to obtain the data, and provides the data to the ring controller 11.

Figure 7:
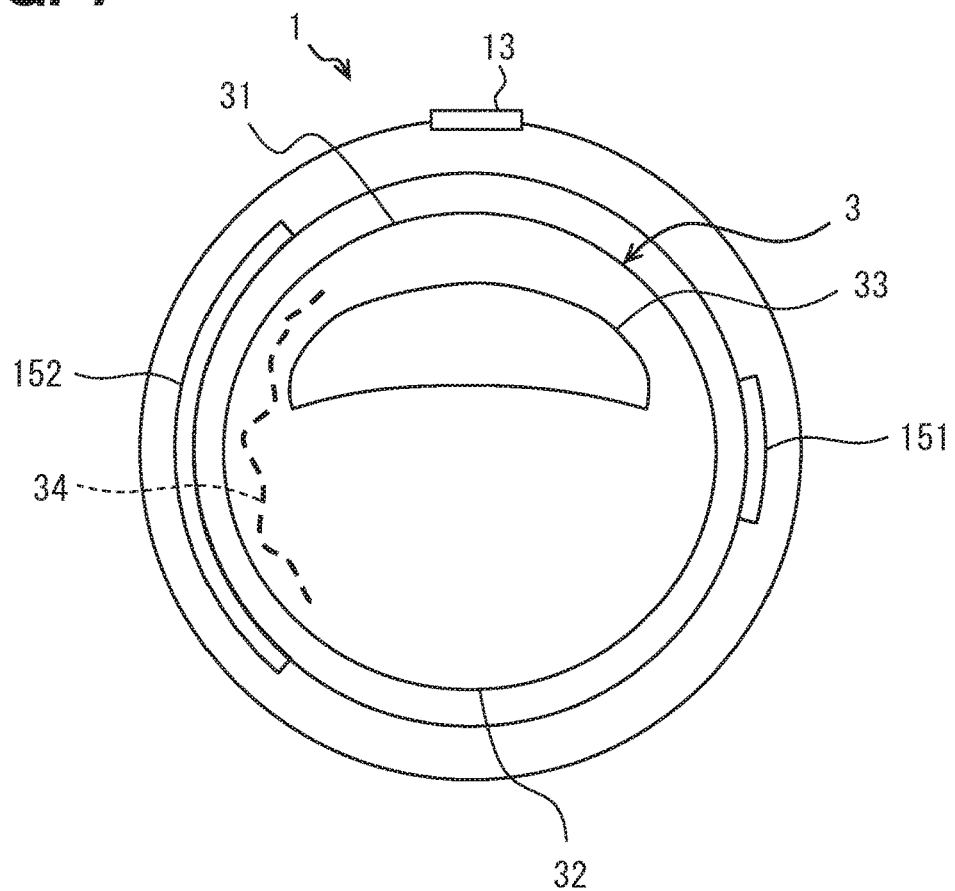
FIG. 7 is a conceptual diagram showing an example of arrangement of a light emitting module and an imaging module.
Figure 8:
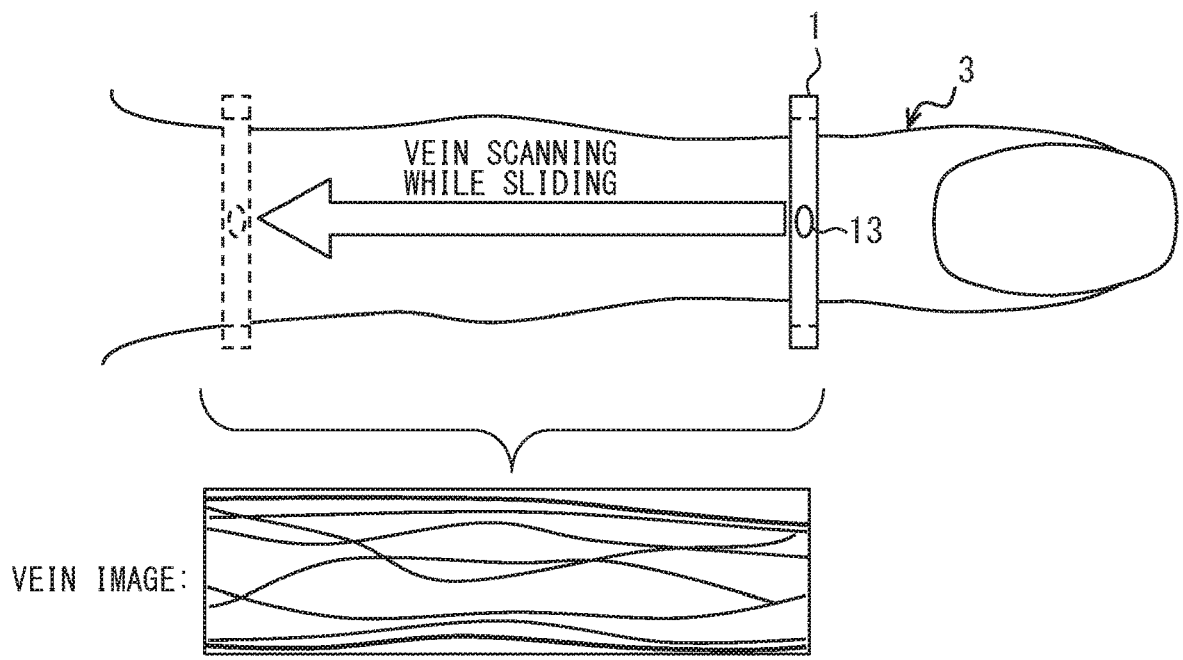
FIG. 8 is a diagram showing a method of using the smart ring.
Figure 9:
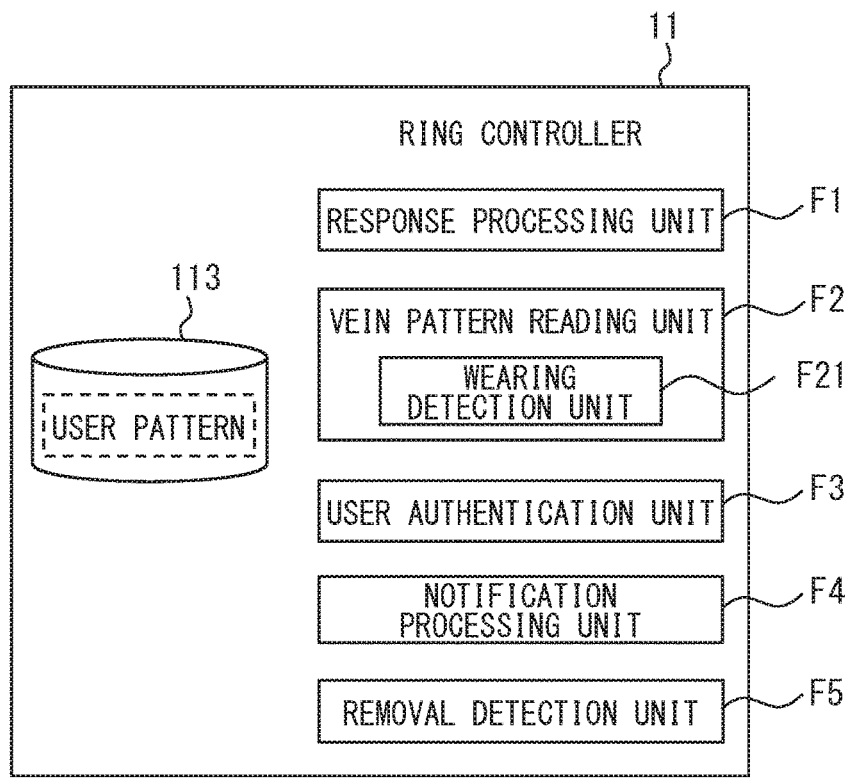
FIG. 9 is a functional block diagram of a ring controller.

The operation unit 13 is a configuration for a user to instruct the smart ring 1 to scan the vein of the finger. That is, the operation unit 13 is configured to allow the user to instruct the reading of the vein pattern. The operation unit 13 can be, for example, a push-type button or the like. The operation unit 13 may also be a pressure sensor or the like. The operation unit 13 is arranged at a predetermined position (for example, an upper end portion) on the outer peripheral surface of the smart ring 1, as shown in FIGS. 7 and 8.

The upper side of the smart ring 1 is a direction corresponding to the back 31 side of the finger 3 when the smart ring 1 is worn in a correct wearing mode. The back 31 of the finger 3 is a surface located on the upper side when the palm is opened and the palm is directed downward. In general, the surface of the finger 3 opposite to the back 31 is also referred to as the pad 32 of the finger 3.

The correct wearing mode of the smart ring 1 is a wearing mode that is assumed when the smart ring 1 is designed, and is set in advance in order to prevent malfunction and inactivation of the smart ring 1. Here, as an example, it is assumed that a mode in which the smart ring 1 is worn in such a manner that the operation unit 13 is located in the center of the back 31 in the width direction in the vicinity of the base of the finger 3 is set as the correct wearing mode. FIG. 7, a reference numeral 33 represents a nail of the finger 3, and a reference numeral 34 represents the vein of the finger 3. In FIG. 7, the illustration of components other than the vein imaging device 15, such as the ring communication module 12, is omitted. However, the operation unit 13 is shown in order to clearly show the vertical direction.

The notification unit 14 is configured to notify the user of predetermined information. The notification unit 14 operates based on instructions from the ring controller 11. The notification unit 14 is realized by using, for example, an LED. The notification unit 14 is arranged, for example, on the outer peripheral surface of the smart ring 1. The notification unit 14 may be a vibrator that generates vibration or a speaker.

The vein imaging device 15 is configured to acquire the vein pattern of the user's finger. The vein imaging device 15 includes a light emitting module 151 and an imaging module 152. The light emitting module 151 is configured to emit light (in other words, electromagnetic waves) having a predetermined wavelength for imaging the vein based on instructions from the ring controller 11.

The light emitting module 151 is realized by using, for example, a light emitting diode (hereinafter, LED) and a drive circuit. The LED is an element that outputs light of a predetermined wavelength. The drive circuit is a circuit that supplies electrical power to the LED to emit light according to instructions from the authentication ECU 21. The light emitting module 151 is provided at a predetermined position on an inner peripheral surface of the smart ring 1. For example, the light emitting module 151 is arranged on the inner peripheral surface of the smart ring 1 at a position where light is emitted toward the side surface portion of the finger (that is, the side surface portion of the inner peripheral surface).

The light having a predetermined wavelength for imaging the vein (hereinafter, detection light) is light having a property of being easily absorbed by the vein. For example, as the detection light, an infrared ray, a near infrared ray, a visible light having a wavelength of 500 nm or more, or the like can be used. Here, as a more preferable aspect, the light emitted by the light emitting module 151 (specifically, the LED) is configured to emit a visible light having a wavelength of 500 nm to 700 nm. According to the configuration in which the light emitting module 151 emits the visible light, the user can visually recognize that the vein scanning function is operating based on the light emitted from the light emitting module 151. As another aspect, the light emitting module 151 may be configured to output an infrared ray or a near infrared ray by using an infrared LED or the like.

The imaging module 152 is an imaging sensor that images the detection light that has passed through the finger 3. The imaging module 152 is realized by using, for example, a plurality of imaging elements. The imaging module 152 is arranged on the inner peripheral surface of the smart ring 1 at a position opposite to the light emitting module 151. That is, the imaging module 152 is arranged in a region substantially facing the light emitting module 151 on the inner peripheral surface of the smart ring 1. The imaging module 152 may be set to have a wide-angle imaging range by using a wide-angle lens or the like.

The vein imaging device 15 is configured such that the light emitting module 151 and the imaging module 152 operate in conjunction with each other. Specifically, the imaging module 152 is configured to perform an imaging process while the light emitting module 151 is emitting the detection light. With such a configuration, the light emitted from the light emitting module 151 toward the side surface portion of the finger passes through the finger 3 and is received by the imaging module 152. Here, since the light emitted by the light emitting module 151 has a property of being absorbed by the vein, the imaging module 152 captures an image showing a structure of the vein. Specifically, since reduced hemoglobin that flows in the vein in the subcutaneous tissue of the finger absorbs the detection light, an image in which a portion corresponding to the vein is shaded is generated. The image generated by the imaging module 152 is sequentially provided to the ring controller 11.

The image captured by the imaging module 152 by one capturing is also referred to as a local vein image hereinafter. The local vein image is an image representing the vein of a local portion where the smart ring 1 is located on the finger of the user. The local vein image represents the vein pattern present in a region of the user's finger facing the imaging module 152 (in other words, an imageable range). The imageable range of the imaging module 152 is determined according to a width of the imaging module 152 and the length of the imaging module 152 in the inner circumferential direction. The local vein image captured by the vein imaging device 15 is combined into a continuous image by the ring controller 11.

In the present embodiment, as an example, the vein imaging device 15 is configured as a so-called transmitted light imaging type vein imaging device that acquires a vein pattern by imaging transmitted light, but is not limited to this. The vein imaging device 15 may be configured as a reflected light imaging type vein imaging device that acquires a vein pattern by imaging reflected light.

The battery 16 is a battery that stores electric power used for the operation of the smart ring 1. The battery 16 is realized by using a chargeable and dischargeable battery (that is, a secondary battery). The battery 16 is electrically connected to electrical components of the smart ring 1 and supplies an electric power for driving to the electrical components.

The wireless charging receiver 17 is configured to receive the electric power transmitted from the wireless charger 28 and charge the battery 16. The wireless charging receiver 17 includes a secondary coil and a power receiving circuit. The secondary coil is configured to be electromagnetically coupled to the primary coil included in the wireless charger 28 to receive the electric power wirelessly transmitted from the wireless charger 28. The power receiving circuit converts the electric power received by the secondary coil into a direct-current voltage suitable for charging the battery 16.

Next, functions of the ring controller 11 will be described. The ring controller 11 includes a response processing unit F1, a vein pattern reading unit F2, a user authentication unit F3, a notification processing unit F4, and a removal detection unit F5 as functional blocks realized by the MPU 111 executing the above-described electronic key program. Some or all of the functions of the ring controller 11 may be realized as hardware. A configuration in which a certain function is realized as hardware includes a configuration in which the function is realized by use of one or more ICs or the like.

The response processing unit F1 cooperates with the ring communication module 12 to execute a process of generating a response signal to a signal transmitted from the in-vehicle system 2 and returning the response signal. For example, when the response processing unit F1 receives the challenge signal from the in-vehicle system 2, the response processing unit F1 generates a response signal including a response code generated using the encryption key registered in the flash memory 113 in advance. The response signal generated by the response processing unit F1 is output to the ring communication module 12 and is transmitted as a wireless signal. The response processing unit F1 corresponds to an authentication response unit. The response processing unit F1 corresponds to a configuration that cooperates with the ring communication module 12 to perform data communication with the in-vehicle system 2. The type of signal generated by the response processing unit F1 is not limited to the above.

The response processing unit F1 (and thus the ring controller 11) of the present embodiment has a response mode and a non-response mode as operation modes. The response mode is an operation mode in which the response signal is generated and returned in response to the challenge signal transmitted from the in-vehicle system 2. On the other hand, the non-response mode is an operation mode in which the response signal is not returned even when the challenge signal transmitted from the in-vehicle system 2 is received. The operation mode of the response processing unit F1 is determined according to the authentication result of the user authentication unit F3.

The response processing unit F1 operates in the response mode when the user authentication unit F3 described later determines that a person wearing the smart ring 1 (hereinafter, referred to as a wearer) is a regular user. Further, the response processing unit F1 operates in the non-response mode when the user authentication unit F3 does not determine that the wearer person is a regular user. A case where the user authentication unit F3 does not determine that the wearer is a regular user includes a state in which the smart ring 1 is not worn on any finger (in other words, the state in which the smart ring 1 is removed). That is, when the smart ring 1 is not worn on any finger or when the user authentication unit F3 determines that the wearer is not a regular user as a result of the user authentication process described later, the response processing unit F1 becomes the non-response mode.

The vein pattern reading unit F2 cooperates with the vein imaging device 15 to acquire the vein pattern of the user's finger. The vein pattern reading unit F2 corresponds to a wearer information acquisition unit. The vein pattern reading unit F2 executes a vein pattern reading process (scan process) based on, for example, a user operation on the operation unit 13. For example, the vein pattern reading unit F2 continuously causes the vein imaging device 15 to perform the imaging process at predetermined imaging intervals (for example, every 20 milliseconds) while the operation unit 13 is being pressed by the user to acquire a plurality of local vein images. Next, one continuous vein image is acquired by synthesizing the plurality of local vein images as continuous frames. Then, the vein pattern of the finger of the user is acquired by analyzing the vein image. For convenience, a process of acquiring the plurality of continuous local vein images and specifying the vein pattern based on the plurality of local vein images is also referred to as a scanning process.

The synthesizing process performed by the vein pattern reading unit F2 on the plurality of continuous local vein images is, more specifically, a process of connecting (in other words, combining) continuously captured image groups while aligning the images. A variety of methods can be used as a method of combining the images captured continuously. For example, the images are aligned using a SIFT (Scale-Invariant Feature Transform) feature, and the images are combined so that overlapping portions captured at the same place overlap with each other. When combining the adjacent images, it is preferable to perform image processing such as deforming each image so that overlapping portions of the same place overlap with each other. Various algorithms such as an Optical Flow-based algorithm can be used as an algorithm for aligning images.

In the present embodiment, as an example, the vein pattern reading unit F2 sequentially operates the vein imaging device 15 under the condition that the operation unit 13 is pressed by the user, and reads the vein pattern. According to such an aspect, the user can cause the smart ring 1 to read the vein pattern by sliding the smart ring 1 from a fingertip toward a root while pressing the operation unit 13. As another aspect, the vein pattern reading unit F2 may be configured to automatically cause the vein imaging device 15 to sequentially operate until a predetermined time elapses from that time to acquire the vein pattern, when the operation unit 13 is pressed a predetermined number of times (for example, once) by the user.

Further, the smart ring 1 may also be configured to acquire the vein image by using an event other than the user operation on the operation unit 13 as a trigger. For example, a pressure sensor may be provided on the inner peripheral surface of the smart ring 1, and the scanning process may be performed by using the pressure sensor as a trigger.

Further, when the smart ring 1 is configured to include an acceleration sensor, the vein image may be acquired by sequentially operating the vein imaging device 15 for a predetermined time from a time when an output value of the acceleration sensor becomes equal to or higher than a predetermined operation threshold value. The operation threshold may be set to an acceleration that can be observed when the user picks up the smart ring 1 placed on a shelf or a desk. According to such an aspect, the scanning process is executed with the trigger of the user picking up the smart ring 1 placed on the shelf or the desk.

When the smart ring 1 is configured to include a temperature sensor that detects a temperature of the finger of the user, the vein imaging device 15 is sequentially operated to acquire the vein image for a predetermined time after the output value of the temperature sensor becomes equal to or higher than a predetermined body temperature threshold value. The body temperature threshold may be set to, for example, 20° C. in consideration of cold-sensitive constitution. According to such a configuration, when the user wears the smart ring 1, the detection value of the temperature sensor becomes equal to or higher than the body temperature threshold value, and the scanning process is started.

The vein pattern reading unit F2 includes a wearing detection unit F21 as a sub-function. The wearing detection unit F21 is configured to detect a predetermined user operation that functions as a trigger for starting the above-described scanning process. The wearing detection unit F21 corresponds to a configuration that detects a user operation of wearing the smart ring 1 on the finger. As described above, the wearing detection unit F21 may determine that the user operation of wearing the smart ring 1 on the finger is performed, for example, when the operation unit 13 is pressed. Further, the wearing detection unit F21 may determine that the user operation of wearing the smart ring 1 on the finger is performed based on the detection value of the temperature sensor being equal to or higher than the body temperature threshold. The body temperature, the acceleration that acts on the smart ring 1, the pressure that acts on the inner peripheral surface of the smart ring 1, and the like correspond to state quantities that function as an indicator of whether the smart ring 1 is worn by the user.

In the present embodiment, the vein pattern reading unit F2 is configured to acquire a relatively wide range of the vein pattern by synthesizing the plurality of local vein images sequentially captured by the vein imaging device 15 in the process of sliding from the fingertip to the root. As another configuration, the vein pattern reading unit F2 may be configured to extract the vein pattern for user authentication from one local vein image. In that case, the user authentication unit F3 described later performs the user authentication using the vein pattern extracted from the local vein image.

However, in the configuration in which the user authentication is performed using the vein pattern extracted from one local vein image as described above, it is assumed that the amount of vein information that can be used for the authentication process is small and the authentication accuracy is not high. This is because only the vein pattern present in the image capturing range of the imaging module 152 can be used for authentication. In view of such circumstances, it can be expected that the user authentication can be performed more accurately in a case where the user authentication is performed using the vein pattern formed by combining the local vein images captured at the plurality of time points at which the smart ring 1 is worn on the user's finger at different positions, as in the present embodiment. In any of the aspects, it is preferable that the imaging module 152 uses a wide-angle lens or the like to set the imaging range to a wide angle.

The user authentication unit F3 is configured to perform the user authentication by comparing the vein pattern (hereinafter, a scan pattern) read by the vein pattern reading unit F2 with a user pattern registered in the flash memory 113. That is, the user authentication unit F3 is configured to perform the vein authentication process using the user pattern registered in advance. The user authentication unit F3 determines that the wearer is an authorized user when the scan pattern matches the user pattern as a result of the process of comparing the scan pattern and the user pattern (so-called matching process).

The match here is not limited to a perfect match. The user authentication unit F3 may be configured to determine that the scan pattern matches the user pattern when a matching degree of the scan pattern with the user pattern (in other words, the degree of similarity) is equal to or greater than a predetermined threshold. The scan pattern is an example of the wearer information. Also, the user pattern is an example of user information.

Figure 10A:
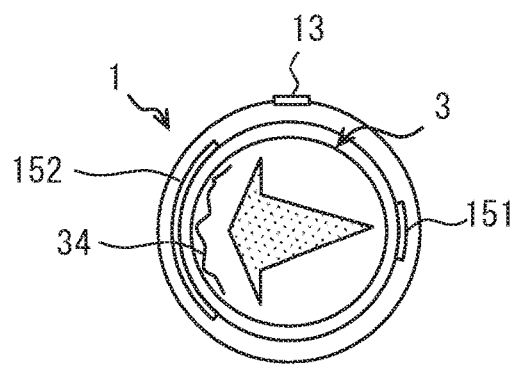
FIG. 10A and FIG. 10B are diagrams for explaining how a user wears the smart ring.
Figure 10B:
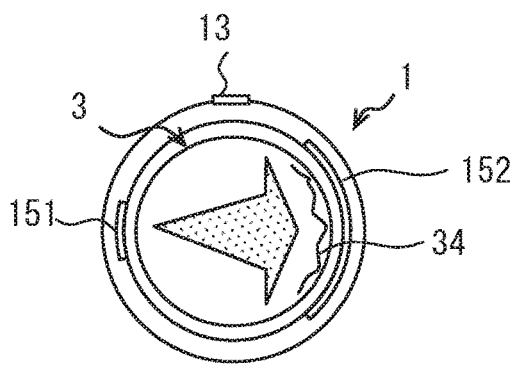

It is preferable that both a vein pattern of a left side surface of the finger 3 and a vein pattern of a right side surface of the finger 3 are registered in the flash memory 113 as user patterns. Since the smart ring 1 has an annular shape, as shown in FIGS. 10A and 10B, the smart ring 1 can be worn on the user's finger even when the left and right are reversed. Further, depending on an external configuration of the smart ring 1, it is assumed that the user has difficulty distinguishing the left and the right of the smart ring 1.

Therefore, it is preferable that the vein pattern on the right side surface of the finger 3 is also registered as a user pattern in the flash memory 113 so that the wearer can be determined as an authorized user even when the user wears the smart ring 1 with the left and right sides reversed. Such a configuration corresponds to a configuration in which a vein pattern for each wearing mode of the smart ring 1 that can be adopted by the user is registered as a user pattern in the flash memory 113.

According to the configuration in which the vein pattern for each wearing mode of the smart ring 1 that can be adopted by the user is registered as the user pattern, the robustness of user authentication process with respect to the method of using the smart ring 1 by the user is improved. As a result, the user can easily use the smart ring 1 without paying attention to the direction of the smart ring 1 and the convenience is improved.

If a plurality of vein patterns are registered in the flash memory 113 as user patterns, the user authentication unit F3 may compare each of the plurality of user patterns with the scan pattern. If any one of the plurality of user patterns matches the scan pattern, the wearer may be determined to be the authorized user. If the scan pattern does not match any of the plurality of user patterns, it may be determined that the wearer is not the authorized user.

The notification processing unit F4 cooperates with the notification unit 14 to execute a process of notifying the user of various information. As elements forming a light emission pattern, the color of light, the number of times of light emission, the presence or absence of blinking, the blinking interval, and the like can be adopted.

For example, when the user authentication unit F3 fails in the user authentication, the notification processing unit F4 causes the notification unit 14 to emit light in a predetermined light emission pattern (hereinafter, authentication failure pattern). This notifies that the user authentication has failed. Further, the notification processing unit F4 causes the notification unit 14 to emit light in a predetermined light emission pattern (hereinafter, authentication success pattern) when the user authentication by the user authentication unit F3 is successful. This notifies that the user authentication has succeeded. The authentication success pattern is configured as a light emission pattern that is visually different from the authentication failure pattern.

In addition, the notification processing unit F4 may be configured to cause the notification unit 14 to emit light in a predetermined light emission pattern when the scanning process is being executed. This notifies the user that the scanning process is being executed. Further, the notification processing unit F4 may be configured to cause the notification unit 14 to emit light in a predetermined light emission pattern when the remaining amount of power of the battery 16 is at a predetermined charge level. This notifies the user that the battery 16 needs to be charged.

The removal detection unit F5 is configured to detect that the user has removed the smart ring 1. The removal detection unit F5 of the present embodiment acquires images by periodically operating the vein imaging device 15 at a predetermined monitoring cycle after the user authentication unit F3 determines that the wearer is the authorized user. Then, when the image captured by the vein imaging device 15 is an image of the user's finger, it is determined that the user wears the smart ring 1. On the other hand, if the captured image is not an image of the user's finger, the removal detection unit F5 determines that the user has removed the smart ring 1. That is, the removal detection unit F5 detects that the user has removed the smart ring 1 from the finger 3 based on the imaging result of the vein imaging device 15.

The image of the user's finger is, for example, an image showing the vein. When the user does not wear the smart ring 1, there is no finger between the light emitting module 151 and the imaging module 152, and the light of the light emitting module 151 directly enters the imaging module 152. Therefore, the brightness of an image captured when the user does not wear the smart ring 1 is higher than the brightness of an image captured when the user wears the smart ring 1. That is, it is possible to determine whether the smart ring 1 is worn on the user's finger also from the brightness distribution of the captured image. The monitoring cycle may be 1 minute, 5 minutes, 30 minutes, or the like.

The method of detecting that the user has removed the smart ring 1 is not limited to the method described above. For example, when a temperature sensor that detects a temperature of the user's finger is provided, the removal detection unit F5 may determine that the user has removed the smart ring 1 based on an output value of the temperature sensor being less than a predetermined body temperature threshold value. Determining that the user has removed the smart ring 1 corresponds to detecting that the user has removed the smart ring 1.

If the smart ring 1 has a function as a pulse wave sensor, the removal detection unit F5 may be configured to detect that the user has removed the smart ring 1 based on a detection result of the pulse wave sensor. The pulse wave sensor is a sensor that sequentially detects a pulse wave signal indicating a change in blood vessel volume according to a user's pulse. The vein imaging device 15 described above can be used as a photoelectric pulse wave sensor that utilizes the absorption characteristics of blood components. As another aspect, the pulse wave sensor may be a bio-impedance type pulse wave sensor that detects a pulse wave signal by flowing a weak current from an electrode.

Alternatively, the removal detection unit F5 may determine that the user has removed the smart ring 1 at a timing when a predetermined expiration time has elapsed from the time when the user authentication unit F3 determines that the wearer is the authorized user. The expiration time may be 12 hours, for example.

Figure 11:
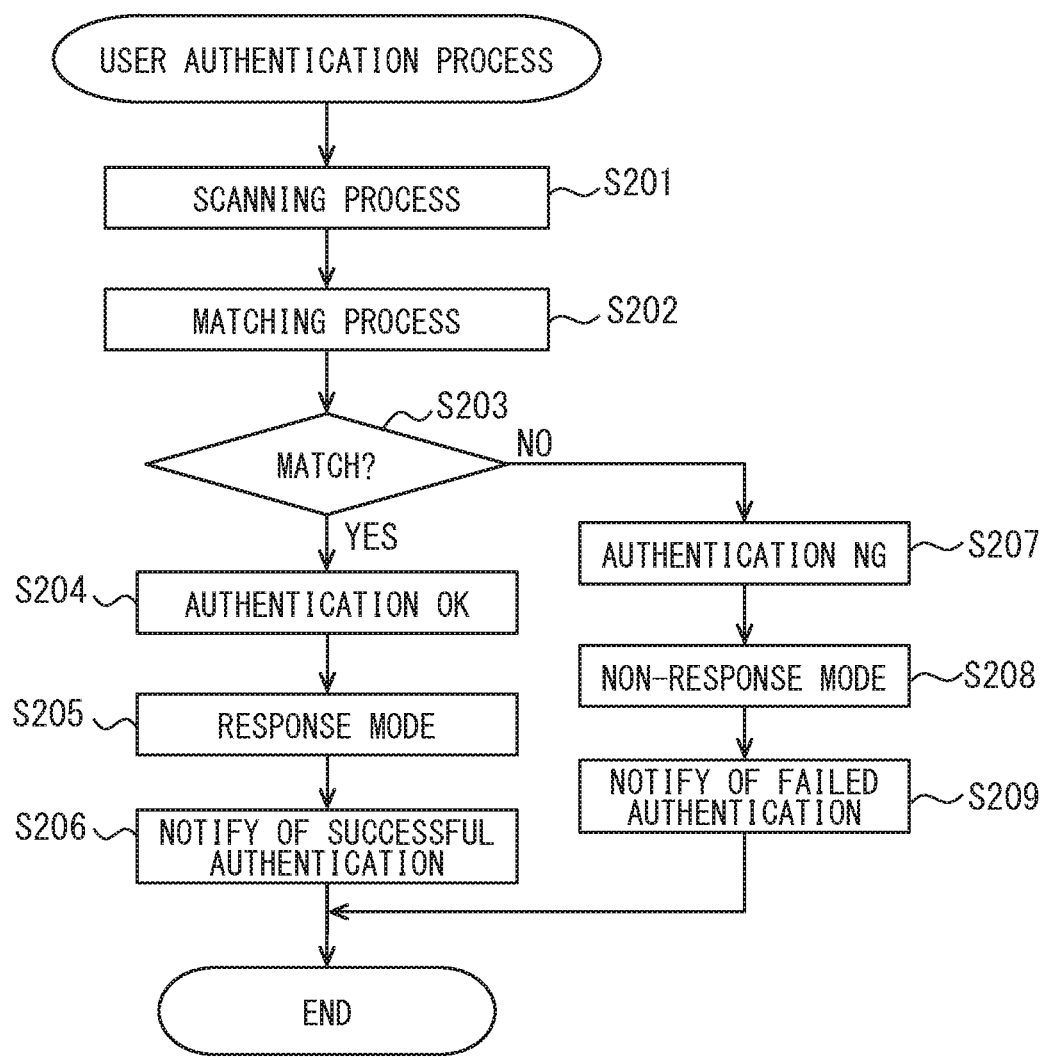
FIG. 11 is a flowchart of an user authentication process performed by the ring controller.

Next, the user authentication process performed by the ring controller 11 of the smart ring 1 will be described using the flowchart shown in FIG. 11. The flowchart shown in FIG. 11 is triggered by the user pressing the operation unit 13, for example. The user authentication process may be started when a predetermined condition for starting the scanning process is satisfied.

In S201, the vein pattern reading unit F2 cooperates with the vein imaging device 15 to perform the scanning process. Then, the vein pattern (that is, the scan pattern) of the wearer is acquired, and the process proceeds to S202. In S202, the user authentication unit F3 performs the matching process between the scan pattern acquired in S201 and the user pattern registered in the flash memory 113, and determines whether the scan pattern matches the user pattern.

When it is determined that the scan pattern matches the user pattern as a result of the matching process in S202, an affirmative determination is made in S203 and the process proceeds to S204. On the other hand, when it is determined that the scan pattern does not match the user pattern as a result of the matching process in S202, a negative determination is made in S203 and the process proceeds to S207.

In S204, the user authentication unit F3 determines that the wearer is the authorized user (that is, the authentication is OK), and the process proceeds to S205. The determination result that the wearer is the authorized user is retained until the removal detection unit F5 determines that the user has removed the smart ring 1. In other words, when the removal detection unit F5 determines that the user has removed the smart ring 1, the determination result that the authorized user wears the smart ring 1 is discarded. The determination result that the wearer is the authorized user may be discarded at a timing when a predetermined expiration time has elapsed from the time when the determination result was obtained.

In S205, the user authentication unit F3 sets the operation mode of the response processing unit F1 to the response mode, and the process proceeds to S206. In S206, the notification processing unit F4 causes the notification unit 14 to emit light in the authentication success pattern, and the present flow ends.

In S207, the user authentication unit F3 determines that the wearer is not the authorized user (that is, authentication NG), and the process proceeds to S208. In S208, the user authentication unit F3 sets the operation mode of the response processing unit F1 to the non-response mode, and the process proceeds to S209. In S209, the notification processing unit F4 causes the notification unit 14 to emit light in the authentication failure pattern and ends the present flow.

According to the above-described embodiment, if the wearer of the smart ring 1 is determined to be the authorized user as a result of the user authentication process using the vein pattern, the smart ring 1 returns the response signal in response to the challenge signal from the in-vehicle system 2. Therefore, when the authorized user wears the smart ring 1, the ring authentication process by wireless communication between the smart ring 1 and the in-vehicle system 2 also succeeds, and smart functions such as unlocking or locking the vehicle door, starting the engine, and the like can be used.

On the other hand, when the wearer is not determined to be the authorized user as a result of the user authentication process, the smart ring 1 does not return the response signal in response to the challenge signal from the in-vehicle system 2. Therefore, even if the third party wears the smart ring 1, the ring authentication process by the in-vehicle system 2 fails, and vehicle control such as unlocking of the vehicle V is not executed.

In addition, according to the above-described embodiment, the result of the user authentication process that the smart ring 1 is worn by the authorized user is discarded when the removal detection unit F5 detects that the user has removed the smart ring 1 from the finger. That is, the result of the user authentication process that the smart ring 1 is worn by the authorized user is valid only while the authorized user wears the smart ring 1.

With such a configuration, even if a third party obtains the smart ring 1 as the electronic key of the vehicle V, since the smart ring 1 does not return the response signal, the vehicle V cannot be used. Therefore, even if the user drops the smart ring 1 or the smart ring 1 is stolen, a risk that the vehicle V is illegally used can be reduced.

By the way, as another configuration for reducing the risk that the vehicle V is illegally used by a third party, a configuration can be assumed in which a biometric authentication device is arranged at a door handle of a vehicle door or a predetermined position in the vehicle compartment, and a user authentication is performed using the biometric authentication device. The biometric authentication device here is a device that authenticates a user by using, for example, a vein pattern of a user's hand or finger, a fingerprint, an iris pattern, a face image, or the like.

Even with such an assumed configuration, it is certainly expected that the risk that the vehicle V is illegally used by a third party can be reduced. However, in the assumed configuration, there is a need of reading biometric information such as a vein or fingerprint by the biometric authentication device mounted on the vehicle V each time the user uses the vehicle V (strictly, each time the smart function is used). Therefore, the assumed configuration may impair the convenience of the user.

On the other hand, in the present embodiment, after the smart ring 1 reads the vein pattern and the vein authentication is successful, the smart ring 1 holds the determination result that the authentication is OK until the smart ring 1 is removed. Therefore, there is no need of reading the biometric information each time the user use the smart function.

In addition, according to the present embodiment, the data transmitted and received between the smart ring 1 and the in-vehicle system 2 when using the smart function is the challenge code and the response code. That is, the data transmitted and received between the smart ring 1 and the in-vehicle system 2 is similar to a data in a conventional electronic key system. Therefore, the user can use the smart function with the same responsiveness as the conventional electronic key system. That is, according to the above configuration, it is possible to enhance the crime prevention performance of the vehicle V while maintaining the convenience for the user.

In the vehicle electronic key system according to the present embodiment, the authentication process for the user to use the smart function is performed in two stages. That is, the vehicle electronic key system execute a first authentication process for authenticating the wearer of the smart ring 1 using the vein pattern of the user, and a second authentication process for authenticating the smart ring 1 as the communication partner by the authentication ECU 21 using the predetermined encryption key. Then, the authentication ECU 21 develops the smart function only when both the first authentication process and the second authentication process are successful. That is, in the above-described vehicle electronic key system, since the authentication ECU 21 is configured to perform the vehicle control as the smart function after performing two-step authentication, it is possible to enhance the crime prevention performance compared with the conventional vehicle electronic key system.

In addition, in the present embodiment, the user authentication is performed by the vein authentication process. It is generally said that vein authentication is less likely to be forged than fingerprint authentication. Further, the vein pattern is unlikely to change with time, and thus the vein authentication is less likely to be affected over time, while the fingerprint authentication is susceptible to the secular change of the fingerprint. That is, as in the above-described embodiment, the configuration in which biometric authentication is performed using the vein pattern can have higher crime prevention performance and higher authentication accuracy than the configuration in which biometric authentication is performed using a fingerprint.

While the embodiments of the present disclosure have been described above, the present disclosure is not limited to the embodiments described above, and various modifications to be described below are included in the technical scope of the present disclosure, and may be implemented by various modifications within a scope not departing from the spirit described below. For example, various modifications to be described below can be implemented in combination as appropriate within a scope that does not cause technical inconsistency.

Note that members having the same functions as those described in the above embodiment are denoted by the same reference numerals, and a description of the same members will be omitted. Further, when referring to only a part of the configuration, the configuration of the embodiment described above can be applied to other portions.

First Modification

Figure 12:
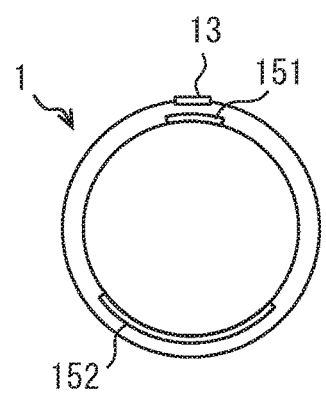
FIG. 12 is a conceptual diagram showing another example of arrangement of the light emitting module and the imaging module.

In the above-described embodiment, the vein imaging device 15 includes the light emitting module 151 and the imaging module 152 provided so as to capture the vein located on the side surface of the user's finger. However, the arrangement of the light emitting module 151 and the imaging module 152 can be changed as appropriate. For example, the light emitting module 151 and the imaging module 152 may be provided so as to capture an image of a vein near the pad of the user's finger. That is, the imaging module 152 may be extended along a circumferential direction at a lower end of the inner peripheral surface of the smart ring 1 as shown in FIG. 12.

Figure 13:
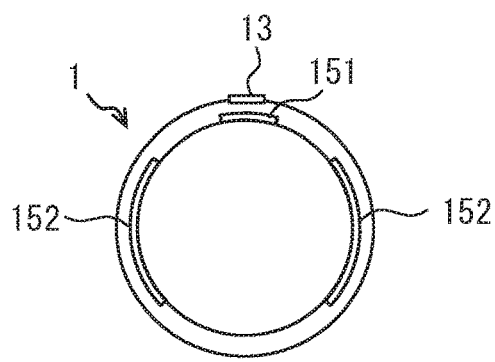
FIG. 13 is a conceptual diagram showing another example of arrangement of the light emitting module and the imaging module.

The light emitting module 151 may not be provided at a position facing the imaging module 152. In other words, the light emitting module 151 may be provided at a position that does not face the imaging module 152. In addition, a plurality of light emitting modules 151 may be provided. A plurality of imaging modules 152 may also be provided. For example, as shown in FIG. 13, one imaging module 152 may be provided on the left and another imaging module 152 may be provided on the right so that images of both side surfaces of the user's finger can be captured. In FIG. 12 and FIG. 13, the ring communication module 12 and the like are not shown.

Second Modification

The position of the ring communication module 12 in the smart ring 1 can be changed appropriately. For example, the ring communication module 12 may be arranged at the lower end of the smart ring 1 or may be arranged at the upper end of the smart ring 1. Further, the ring communication module 12 may be arranged at each of the upper end and the lower end of the smart ring 1. Generally, radio waves used for near-field communication are more easily affected by the human body than radio waves in the LF band. Therefore, it is preferable that the ring communication module 12 included in the smart ring 1 and the in-vehicle communication module 25 included in the in-vehicle system 2 are configured to be capable of wirelessly communicating with each other without via the human body.

Figure 14:
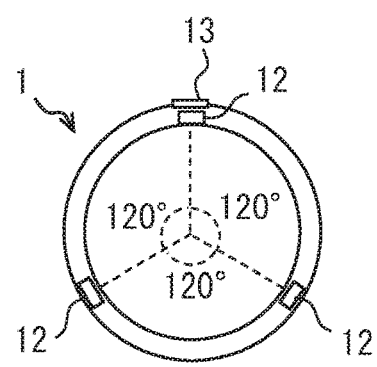
FIG. 14 is a conceptual diagram showing an example of arrangement of ring communication modules.

Further, since the smart ring 1 has an annular shape, the smart ring 1 can rotate while being worn on the finger of the user. As shown in FIG. 14, three ring communication modules 12 may be provided at positions displaced by about 120 degrees in the smart ring 1 so that the smart ring 1 and the in-vehicle system 2 can easily perform wireless communication even if the smart ring 1 rotates. In FIG. 14, the light emitting module 151, the imaging module 152, and the like are not shown.

Third Modification

Figure 15:
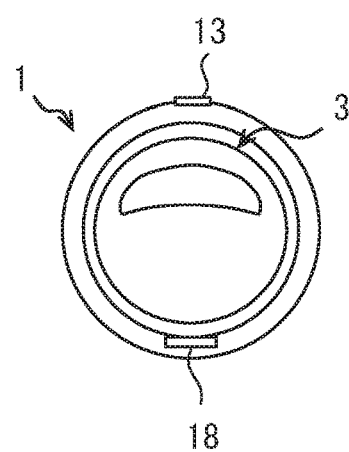
FIG. 15 is a conceptual diagram showing an example of arrangement of an image pickup module in a smart ring according to a third modification.
Figure 16:
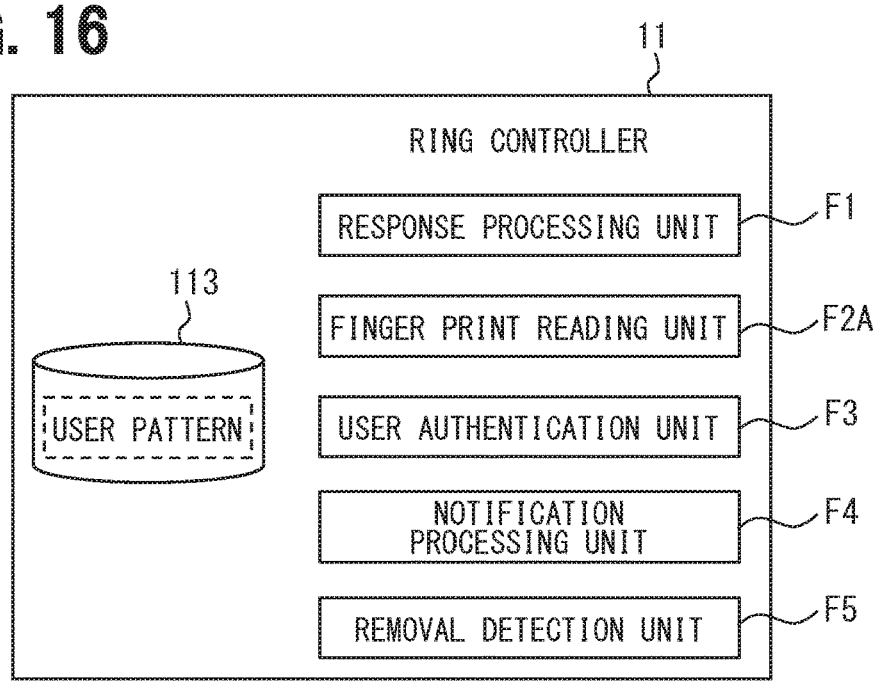
FIG. 16 is a functional block diagram of a ring controller according to a third modification.

In the above-described embodiment, the configuration in which the user authentication is performed using the vein pattern of the finger is disclosed, but the present disclosure is not limited to the above-described configuration. As another configuration, the smart ring 1 may be configured to perform a user authentication using fingerprint information of a finger on which the smart ring 1 is worn. The fingerprint information here is not limited to a skin pattern of a fingertip. The fingerprint information may include a skin pattern on a pad from a first joint to a second joint of the finger and a skin pattern on a pad from the second joint to a third joint of the finger. Hereinafter, an example of a configuration corresponding to the above-described technical idea will be described as a third modification. FIG. 15 and FIG. 16 are conceptual diagrams showing the configuration of the smart ring 1 according to the third modification.

The smart ring 1 according to the third modification includes an in-camera 18 which is a camera for capturing a fingerprint. The in-camera 18 is configured to capture an image of a pad of the user's finger. For example, the imaging module 152 is arranged upward at the lower end of the inner peripheral surface of the smart ring 1 as shown in FIG. 15. The in-camera 18 may be a normal camera (for example, a CCD camera) as long as it can capture a fingerprint. The in-camera 18 is preferably realized by using a wide-angle camera so that a wider range of the pad can be captured. Since it is not necessary to image the vein in this modification, the light emitting module 151 may not be provided. The in-camera 18 is an example of an imaging device.

In addition, the ring controller 11 of the third modification includes a fingerprint reading unit F2A instead of the vein pattern reading unit F2. The fingerprint reading unit F2A is configured to acquire fingerprint information based on the image captured by the in-camera 18. The reading of the fingerprint information itself can be performed by a method similar to the method of reading of the vein pattern. The fingerprint reading unit F2A corresponds to the wearer information acquisition unit. In the flash memory 113 of the third modification, fingerprint information of the authorized user may be registered in advance as a user pattern instead of the vein pattern. The configuration described above also achieves effect similar to the effects of the above-described embodiment.

Fourth Modification

In the above, the configurations in which the user authentication are performed using the finger vein pattern or the fingerprint information have been disclosed. However, the present disclosure is not limited to those configurations. For example, the smart ring 1 may be configured to perform a user authentication using finger shape information. For example, the shape of the finger may be represented by a plurality of types of predetermined feature quantities, and the user authentication may be performed using the feature quantities. As the feature quantities representing the shape of the finger, joint spacing, thickness of each part, curvature degree near the first and second joints, wrinkle pattern, and the like can be adopted.

Fifth Modification

In the above-described embodiment and modifications, the smart ring 1 performs user authentication. However, the function of authenticating the user using the biometric information of the user's finger may also be provided to the authentication ECU 21. Hereinafter, an example of a configuration corresponding to the above-described technical idea will be described as a fifth modification.

Figure 17:
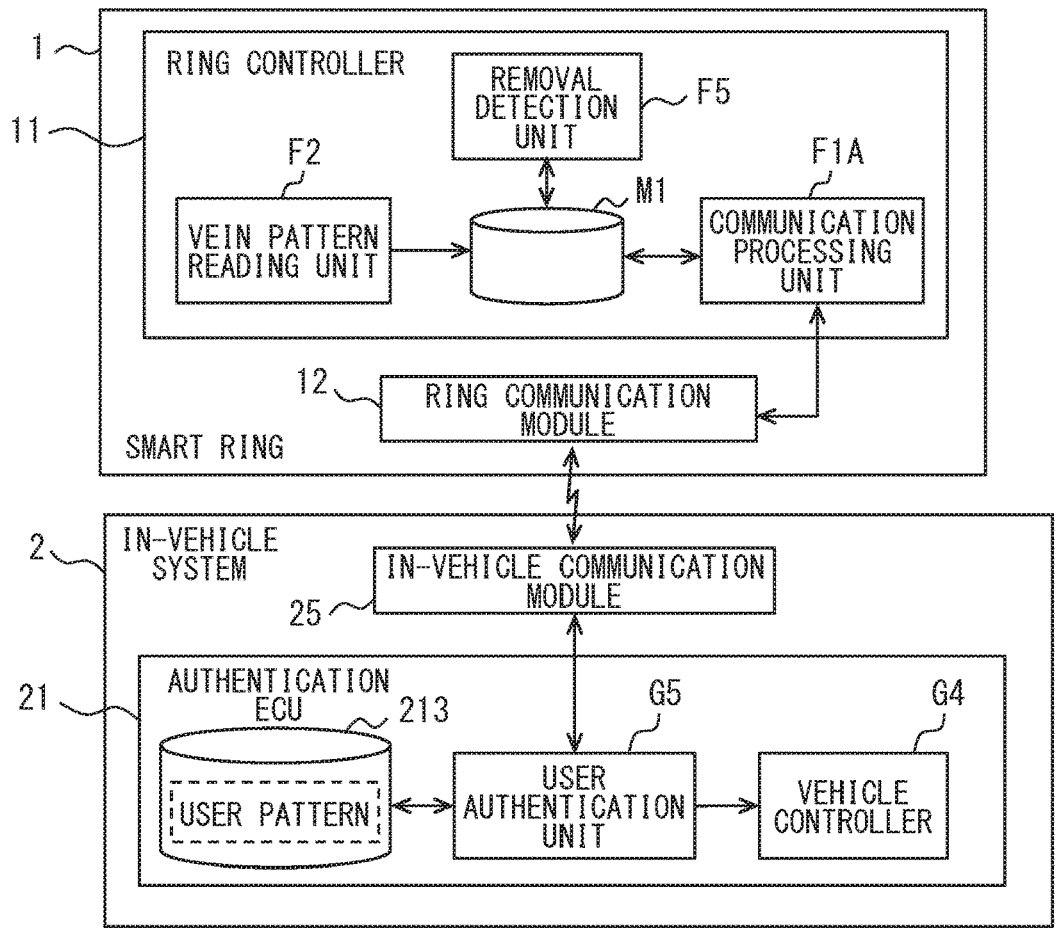
FIG. 17 is a block diagram showing a configuration of a vehicle electronic key system according to a fifth modification.

As shown in FIG. 17, the ring controller 11 of the fifth modification includes a communication processing unit F1A, a vein pattern reading unit F2, a removal detection unit F5, and a reading result holding unit M1. The vein pattern reading unit F2 is the same as in the above-described embodiment. The vein pattern reading unit F2 stores the read vein pattern (that is, the scan pattern) in the reading result holding unit M1.

The reading result holding unit M1 is configured to temporarily hold the scan pattern. For example, the reading result holding unit M1 can be realized by using a part of the storage area included in the RAM 112 or the flash memory 113. The reading result holding unit M1 may be realized by using a rewritable functional medium. The reading result holding unit M1 is an example of a storage.

The communication processing unit F1A is configured to cooperate with the ring communication module 12 to perform data communication with the in-vehicle system 2. The communication processing unit F1A cooperates with the ring communication module 12 to transmit the scan pattern stored in the reading result holding unit M1 to the in-vehicle system 2. The timing of transmitting the scan pattern may be, for example, when a signal requesting a transmission of the reading result is received from the in-vehicle system 2. The scan pattern stored in the reading result holding unit M1 may be deleted when the removal detection unit F5 detects that the user has removed the smart ring 1, or when the predetermined expiration time has elapsed.

When the scan pattern is not stored in the reading result holding unit M1, the notification processing unit F4 of the present modification causes the notification unit 14 to emit light with a predetermined light emission pattern (hereinafter, unscanned pattern) indicating that state. In addition, when the scan pattern is stored in the reading result holding unit M1 as a result of the scanning process, the notification processing unit F4 causes the notification unit 14 to emit light in a predetermined light emission pattern (hereinafter, a scan success pattern) indicating that state. The successful scan pattern and the unscanned pattern are set to light emission patterns having different light colors and the like.

The authentication ECU 21 of the fifth modification includes a vehicle controller G4 and a user authentication unit G5. Further, the authentication ECU 21 includes a vehicle information acquisition unit G1, a vehicle state determination unit G2, and a ring authentication unit G3 as a more preferable aspect. The user pattern is registered in the flash memory 213. In the fifth modification, the flash memory 213 is an example of the user information storage.

The vehicle controller G4 is configured to perform a predetermined vehicle control based on the state of the vehicle V at the time of successful authentication and user operation when the authentication process by the user authentication unit G5 is successful. The contents disclosed in the above-described embodiment can be applied to the contents of vehicle control and the like.

The user authentication unit G5 is configured to perform the user authentication by comparing the user pattern registered in the flash memory 113 with the scan pattern provided by the smart ring 1. That is, the user authentication unit G5 is configured to perform the vein authentication process using the user pattern registered in the flash memory 213 in advance.

When a predetermined user authentication start condition is satisfied, the user authentication unit G5 cooperates with the in-vehicle communication module 25 and transmits a signal requesting the smart ring 1 to transmit the scan pattern (hereinafter, a reading result request signal). As an example, the user authentication unit G5 of the fifth modification is configured to transmit the reading result request signal when the ring authentication process by the ring authentication unit G3 is successful.

As another aspect, the user authentication unit G5 may be configured to transmit the reading result request signal at the timing when the communication connection between the in-vehicle communication module 25 and the ring communication module 12 is established. The success of the ring authentication process by the ring authentication unit G3 and the establishment of the communication connection with the smart ring 1 can be adopted as the user authentication start condition.

Then, the user authentication unit G5 performs a matching process between the scan pattern returned from the smart ring 1 as a response to the reading result request signal and the user pattern. As a result of the matching process, when the scan pattern matches the user pattern, the user authentication unit G5 determines that the wearer is the authorized user. On the other hand, when the scan pattern does not match the user pattern, the user authentication unit G5 determines that the wearer is not the authorized user.

According to the above configuration, the user data only needs to be held by the authentication ECU 21, and the smart ring 1 does not need to hold the user data. In addition, since the authentication ECU 21 performs the vein pattern matching process (that is, the vein authentication process), the computing ability required for the smart ring 1 can be suppressed. That is, the configuration of the smart ring 1 can be simplified.

In addition, the smart ring 1 previously reads the vein pattern when the user wears the smart ring 1, and transmits the scan pattern based on the request from the authentication ECU 21. With such a configuration, it is not necessary to perform the vein pattern scanning process at the moment when the user tries to use the smart function of the vehicle V. Therefore, as in the above-described embodiment, the user can use the smart function with the same responsiveness as the conventional electronic key system.

In the above-described configuration, the smart ring 1 transmits the scan pattern after the authentication ECU 21 authenticates the smart ring 1 as a communication partner. However, the present disclosure is not limited to this configuration. The smart ring 1 may also be configured to transmit the scan pattern after the smart ring 1 authenticates that the communication partner of the sing communication module 12 is the authentication ECU 21. That is, the smart ring 1 may have the function of authenticating that the communication partner by near-field communication is a reliable device. With such a configuration, it is possible to reduce the risk that the smart ring 1 will transmit the scan pattern as the biometric information of the user to a suspicious terminal. As described above, the configurations disclosed in the above-described embodiment, the first to fourth modifications, and the sixth to eighth modifications described later can be applied to the fifth modification.

Sixth Modification

In the above-described embodiment and modifications, the near-field communication is adopted as the communication system between the smart ring 1 and the authentication ECU 21. However, the communication system between the smart ring 1 and the authentication ECU 21 may be other than near-field communication. The smart ring 1 and the authentication ECU 21 may perform wireless communication in conformity with short-range wireless communication standards (hereinafter, short-range communication) such as Bluetooth (registered trademark), Wi-Fi (registered trademark), and ZigBee (registered trademark). Short-distance communication is wireless communication in which the communicable distance can be set to 10 meters or more, for example. Near-field communication and short-range communication differ in the communicable distance. Near-field communication refers to a communication by a communication system in which a communication distance is sufficiently smaller than short-range communication.

Seventh Modification

In the above, the configurations in which the present disclosure is applied to the electronic key system for a vehicle, that is, the configurations in which the protection object is the vehicle V have been described. However, the present disclosure is not limited to these configurations. The present disclosure can also be applied to an electronic key systems for a house or an office. That is, the protection object may be a facility such as a house or an office. Further, the protection object may be a safe, a locker, or the like. The present disclosure can be applied to anything that is used with a key.

Eighth Modification

In the above-described configurations, the wearable device that function as the electronic key (that is, the wearable key devices) is the ring type. However, the wearable key device may be other than the ring type.

For example, the wearable key device may be a wristband type or a wristwatch type wearable device that is used by being worn on the user's wrist. The wristband type wearable device as the wearable key device may be configured to perform a user authentication using biometric information (for example, vein pattern) of the user's wrist. The same can be applied to the case of the wristwatch type.

The wearable key device may also be a glasses-type wearable device that is used by being worn on the user's face. In that case, the glasses-type wearable device as the wearable key device may be configured to perform a user authentication using the biometric information (for example, an iris or a face image) of the user's face.

Software stored in a tangible memory and a computer executing the software, only the software, only hardware, or combination of them may be possible to provide the methods or the functions provided by the ring controller 11 of the smart ring 1. For example, when the ring controller 40 is provided by an electronic circuit being hardware, it may be possible to provide by a digital circuit including multiple logic circuits or analog circuits. The same can be applied to the authentication ECU 21.

The authentication ECU 21 may be provided by one computer or a plurality of computer resources configured to be capable of mutual communication. When executed by a controller, the program causes the controller to function according to the description provided herein and causes the controller to perform the method described herein.

What is claimed is:

1. A wearable key device having a ring shape and configured to be used while being worn on a finger, the wearable key device comprising:
    a ring communication module configured to wirelessly communicate with an authentication device provided to a predetermined protection object;
    an imaging device disposed on a side portion of an inner surface of a ring and configured to capture an image of a vein of a side surface of the finger;
    a user information storage storing both a vein pattern of a right side surface and a vein pattern of a left side surface of the finger of an authorized user as user information; and
    a ring controller configured to:
        cooperate with the ring communication module and transmit, to the authentication device, authentication information that is information for certifying that the wearable key device is a key of the protection object;
        acquire a scan pattern indicating a vein pattern of the side surface of the finger of a wearer who wears the wearable key device based on the image captured by the imaging device; and
        compare the scan pattern indicating the vein pattern of the side surface of the finger of the wearer and the user information stored by the user information storage to determine whether the wearer is the authorized user, wherein
    the ring controller is further configured to transmit the authentication information in response to a request from the authentication device when determining that the wearer is the authorized user, and not to transmit the authentication information when not determining that the wearer is the authorized user.

2. The wearable key device according to claim 1, further comprising an operation member configured to receive an operation by the wearer for reading the vein pattern, wherein the imaging device is further configured to sequentially capture the images at a predetermined imaging interval in response to the operation to the operation member, and the ring controller is further configured to generate the scan pattern by synthesizing the images sequentially captured by the imaging device.

3. The wearable key device according to claim 1, wherein the ring controller is further configured to:

detect that the wearer has removed the wearable key device based on the image captured by the imaging device or a detection result of a sensor that detects a stated amount as an index of whether the wearer wears the wearable key device; and discard a determination that the wearer is the authorized user when detecting that the wearer has removed the wearable key device.

4. The wearable key device according to claim 1, further comprising at least one of vibrator or light emitter configured to notify an authentication result of the ring controller.

5. The wearable key device according to claim 1, wherein the ring communication module is further configured to perform near-field communication.

6. The wearable key device according to claim 1, wherein the ring controller includes a ring processor and a ring memory, and the ring memory stores instructions to be executed by the ring processor.

7. An electronic key system comprising a wearable key device having a ring shape and configured to be used while being worn on a finger and an authentication device configured to be provided to a predetermined protection object, wherein the wearable key device includes:

a ring communication module configured to perform wireless communication with the authentication device;

an imaging device disposed on a side portion of an inner surface of a ring and configured to capture an image of a vein of a side surface of the finger; and a ring controller configured to acquire a scan pattern indicating a vein pattern of the side surface of the finger of a wearer who wears the wearable key device based on the image captured by the imaging device and transmit the scan pattern to the authentication device by cooperating with the ring communication module, the authentication device is connected with an authentication side communication module configured to perform the wireless communication with the wearable key device, and the authentication device includes:

a user information storage storing both a vein pattern of a right side surface and a vein pattern of a left side surface of the finger of an authorized user as user information; and an authentication processor configured to acquire the scan pattern from the wearable key device by cooperating with the authentication side communication module, determine whether the wearer is the authorized user by comparing the scan pattern indicating the vein pattern of the side surface of the finger of the wearer and the user information stored by the user information storage, and perform a predetermined control to use the protection object when determining that the wearer is the authorized user.

8. The electronic key system according to claim 7, wherein the wearable key device further includes an operation member configured to receive an operation by the wearer for reading the vein pattern, the imaging device is further configured to sequentially capture the images at a predetermined imaging interval in response to the operation to the operation member, and the ring controller is further configured to generate the scan pattern by synthesizing the images sequentially captured by the imaging device, includes a storage temporarily holding the scan pattern, and is further configured to transmit the scan pattern temporarily held by the storage to the authentication device in response to a request from the authentication device.

9. The electronic key system according to claim 8, wherein the ring controller is further configured to:

detect that the wearer has removed the wearable key device based on the image captured by the imaging device or a detection result of a sensor that detects a stated amount as an index of whether the wearer wears the wearable key device; and discard the scan pattern temporarily held by the storage when detecting that the wearer has removed the wearable key device.

10. The electronic key system according to claim 8, further comprising at least one of vibrator or light emitter configured to notify whether the scan pattern is held by the storage.

11. The electronic key system according to claim 7, wherein the protection object is a vehicle.

12. The electronic key system according to claim 7, wherein the wearable key device and the authentication device are configured to perform near-field communication.

13. The electronic key system according to claim 7, wherein the ring controller includes a ring processor and a ring memory, the ring memory stores instructions to be executed by the ring processor, the authentication device further includes an authentication memory, and the authentication memory stores instructions to be executed by the authentication processor.

14. A wearable key device having a ring shape and configured to be used while being worn on a finger, the wearable key device comprising:

a ring communication module configured to wirelessly communicate with an authentication device provided to a predetermined protection object, the authentication device storing both a vein pattern of a right side surface and a vein pattern of a left side surface of the finger of an authorized user;

an imaging device disposed on a side portion of an inner surface of a ring and configured to capture an image of a vein of a side surface of the finger; and a ring controller configured to acquire a scan pattern indicating a vein pattern of the side surface of the finger of a wearer who wears the wearable key device based on the image captured by the imaging device and transmit the scan pattern indicating the vein pattern of the side surface of the finger of the wearer as information for determining whether the wearer is an authorized user to the authentication device by cooperating with the ring communication module.

15. The wearable key device according to claim 14, wherein the ring controller includes a ring processor and a ring memory, and the ring memory stores instructions to be executed by the ring processor.

16. The wearable key device according to claim 14, wherein the ring controller is further configured to compare the scan pattern indicating the vein pattern of the side surface of the finger of the wearer and the vein pattern of the right side surface and the vein pattern of the left side surface of the finger of the authorized user stored by the authentication device to determine whether the wearer is the authorized user.

\* \* \* \* \*